(12) United States Patent
Cornelius et al.

(10) Patent No.: US 9,934,372 B1
(45) Date of Patent: Apr. 3, 2018

(54) TECHNOLOGIES FOR PERFORMING ORIENTATION-INDEPENDENT BIOIMPEDANCE-BASED USER AUTHENTICATION

(71) Applicant: Intel Corporation, Santa Clara, CA (US)

(72) Inventors: Cory Cornelius, Portland, OR (US); Micah J. Sheller, Hillsboro, OR (US); Jason Martin, Beaverton, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/476,995

(22) Filed: Apr. 1, 2017

(51) Int. Cl.
*G06F 21/32* (2013.01)
*A61B 5/05* (2006.01)
*A61B 5/053* (2006.01)
*A61B 5/117* (2016.01)
*A61B 5/00* (2006.01)

(52) U.S. Cl.
CPC ............ *G06F 21/32* (2013.01); *A61B 5/0536* (2013.01); *A61B 5/117* (2013.01); *A61B 5/0024* (2013.01); *A61B 5/6803* (2013.01)

(58) Field of Classification Search
CPC ... A61B 3/113; A61B 5/4884; A61B 5/02055; A61B 5/486; A61B 5/6803; A61B 5/0024; A61B 18/1492; A61B 18/02; A61B 18/1815; A61B 18/06; A61B 18/18; A61B 18/24; A61B 90/37; A61B 3/14; A61B 3/0025; A61B 5/117; A61B 5/0536; A61N 1/36014; A61N 7/02; A61F 7/007; A61M 5/00; G06F 21/32
See application file for complete search history.

(56) References Cited

U.S. PATENT DOCUMENTS

| | | | |
|---|---|---|---|
| 9,375,145 B2 * | 6/2016 | Chin | A61B 5/0015 |
| 2007/0237365 A1 * | 10/2007 | Monro | A61B 5/1171 382/115 |
| 2013/0131465 A1 * | 5/2013 | Yamamoto | A61B 5/7271 600/301 |
| 2014/0300490 A1 | 10/2014 | Kotz et al. | |
| 2016/0242673 A1 * | 8/2016 | Grychtol | A61B 5/0536 |
| 2017/0231490 A1 * | 8/2017 | Toth | A61B 3/113 600/558 |

* cited by examiner

*Primary Examiner* — Brian Miller
(74) *Attorney, Agent, or Firm* — Barnes & Thornburg LLP

(57) ABSTRACT

Technologies for performing orientation-independent bioimpedance-based user authentication include a compute device. The compute device includes a plurality of electrodes usable to transmit an alternating current and measure a bioimpedance in a section of the body of a user. The compute device is to transmit, with a pair of the electrodes, an alternating current through the section of the body of the user, measure, with a pair of the electrodes, a bioimpedance of the section of the body to the transmitted alternating current, generate a tomographic image as a function of the measured bioimpedance, identify a position of a fiduciary marker in the tomographic image, rotate the tomographic image to a predefined orientation as a function of the position of the fiduciary marker, extract one or more biometric features from the rotated tomographic image, and perform authentication of the user as a function of the extracted one or more biometric features.

25 Claims, 6 Drawing Sheets

TECHNOLOGIES FOR PERFORMING ORIENTATION-INDEPENDENT BIOIMPEDANCE-BASED USER AUTHENTICATION

BACKGROUND

Biometric systems utilize the physiology and/or behavioral aspects of their users (e.g., human beings) to uniquely identify them. However, many biometric systems require the user to actively present their physiology (e.g., swipe a finger for fingerprint authentication) or their behavior to the system (e.g., sign their name). Furthermore, many biometric systems are unable to continually collect biometric data without intervention by the user (e.g., continual finger swipes). Fortunately, bioimpedance-based biometric systems can reduce the amount of user intervention needed to collect biometric data from a user. Such systems typically utilize a series of electrodes to measure the impedance of the user's body to various frequencies, which together form a unique signature of that user's physiology. However, such bioimpedance-based biometric systems typically lose their ability to accurately collect the biometric data if the orientation of the electrodes changes with respect to the user. Accordingly, while typical bioimpedance-based biometric systems may reduce the amount of intervention from the user to collect biometric data, they can introduce additional inaccuracies that may lead to incorrect identification of the user and cause user authentication errors.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
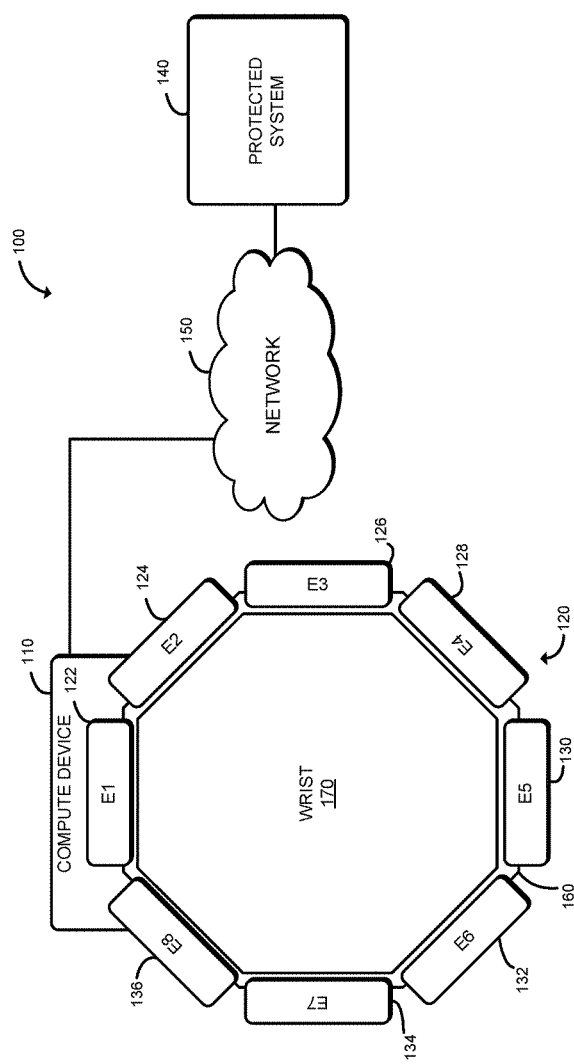
FIG. 1 is a simplified block diagram of at least one embodiment of a system for performing orientation-independent bioimpedance-based user authentication.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

As shown in FIG. 1, an illustrative system 100 for performing orientation-independent bioimpedance-based user authentication includes a compute device 110 in communication with a set 120 of electrodes 122, 124, 126, 128, 130, 132, 134, 136. In the illustrative embodiment, the compute device 110 and the electrodes 120 are connected to a wristband 160 which may be worn around the wrist 170 of a user. In operation, the compute device 110 performs bioimpedance measurement with four or more poles, rather than the typical two poles used in bipolar bioimpedance measurement. By utilizing four or more poles, the compute device 110 obtains sufficient bioimpedance data to generate an image, referred to herein as a tomographic image, of the internal conductivity of the body part at each of multiple frequencies of an alternating current. After generating one or more tomographic images (e.g., a tomographic image for each frequency), the compute device 110 identifies the locations of one or more fiducial markers, such as the locations of one or more bones known to be present in the measured section of the user's body. In the illustrative embodiment, the compute device 110 identifies the locations of the radius and ulna bones in the wrist 170. Afterwards, the compute device 110 compares the identified locations to reference locations (e.g., predefined locations) of those fiducial markers to determine an amount of rotation to apply (e.g., a linear transform with a rotation matrix) to reorient the tomographic images, thereby compensating for any inadvertent rotation of the electrodes about the wrist. Subsequently, the compute device 110 extracts biometric features from the tomographic images (e.g., by calculating statistical features of the tomographic images) and stores the biometric features in a feature vector (e.g., a set of numeric values) for use with authenticating the user (e.g., comparing the feature vector to a reference feature vector, sending the feature vector to a remote compute device for authentication, etc.). The compute device 110 may perform biometric authentication to enable the user to authenticate to the compute device 110 itself (e.g., to access data stored therein) and/or to access a protected system 140, which, in the illustrative embodiment, is in communication with the compute device 110 through a network 150.

Figure 2:
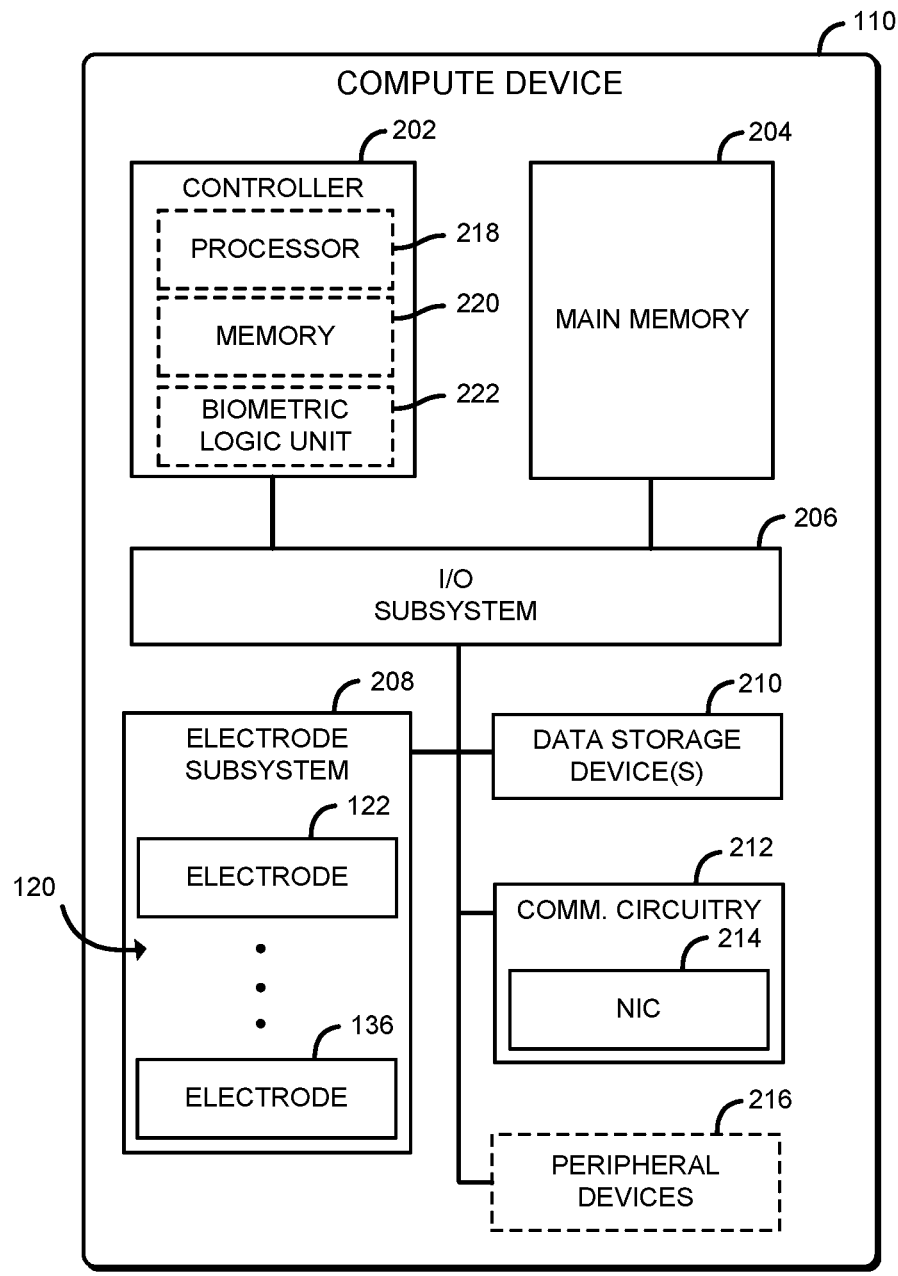
FIG. 2 is a simplified block diagram of at least one embodiment of a compute device of the system of FIG. 1.

Referring now to FIG. 2, the compute device 110 may be embodied as any type of device capable of performing the functions described herein, including transmitting, with a pair of the electrodes 120, an alternating current through a section of the body of the user, measuring, with another pair of the electrodes 120, a bioimpedance of the section of the body to the transmitted alternating current, generating a tomographic image as a function of the measured bioimpedance, identifying a position of a fiduciary marker in the tomographic image, rotating the tomographic image to a predefined orientation as a function of the position of the fiduciary marker, extracting biometric features from the rotated tomographic image, and performing authentication of the user as a function of the extracted biometric features. As shown in FIG. 2, the illustrative compute device 110 includes a controller 202, a main memory 204, an input/output (I/O) subsystem 206, an electrode subsystem 208, one or more data storage devices 210, and communication circuitry 212. Of course, in other embodiments, the compute device 110 may include other or additional components, such as those commonly found in a computer (e.g., display, peripheral devices, etc.). Additionally, in some embodiments, one or more of the illustrative components may be incorporated in, or otherwise form a portion of, another component. For example, in some embodiments, the main memory 204, or portions thereof, may be incorporated in the controller 202.

The controller 202 may be embodied as any type of device capable of performing the functions described herein. As such, the controller 202 may include a single or multi-core processor(s) 218, a microcontroller, or other processor or processing/controlling circuit and a memory 220, which may be embodied as any type of volatile (e.g., dynamic random access memory (DRAM), etc.) or non-volatile memory or data storage capable of performing the functions described herein. In some embodiments, the controller 202 may be embodied as, include, or be coupled to a field programmable gate array (FPGA), an application specific integrated circuit (ASIC), reconfigurable hardware or hardware circuitry, or other specialized hardware to facilitate performance of the functions described herein. Additionally or alternatively, the controller 202 may include a biometric logic unit 222 which may be embodied as any device or circuitry capable of offloading bioimpedance measurement, tomographic image generation, biometric feature extraction, and/or authentication processes from the other components of the controller 202.

The main memory 204 may be embodied as any type of volatile (e.g., dynamic random access memory (DRAM), etc.) or non-volatile memory or data storage capable of performing the functions described herein. In some embodiments, all or a portion of the main memory 204 may be integrated into the controller 202. In operation, the main memory 204 may store various software and data used during operation such as bioimpedance data, tomography data, feature extraction data, operating systems, applications, programs, libraries, and drivers.

The I/O subsystem 206 may be embodied as circuitry and/or components to facilitate input/output operations with the controller 202, the main memory 204, and other components of the compute device 110. For example, the I/O subsystem 206 may be embodied as, or otherwise include, memory controller hubs, input/output control hubs, integrated sensor hubs, firmware devices, communication links (e.g., point-to-point links, bus links, wires, cables, light guides, printed circuit board traces, etc.), and/or other components and subsystems to facilitate the input/output operations. In some embodiments, the I/O subsystem 206 may form a portion of a system-on-a-chip (SoC) and be incorporated, along with one or more of the controller 202, the main memory 204, and other components of the compute device 110, on a single integrated circuit chip. In the illustrative embodiment, the I/O subsystem 206 is at least partially embedded in the wristband 160 of FIG. 1 to enable the transmission of data and/or power to and from the electrodes 120.

The electrode subsystem 208 may be embodied as any device or circuitry for transmitting an alternating current through a pair of the electrodes 120 and measuring the bioimpedance of the user's body with another pair of the electrodes 120. In the illustrative embodiment, each electrode 120 may be embodied as any device capable of transmitting and receiving an alternating electrical current and measuring a bioimpedance (e.g., a phase and a magnitude of an electrical impedance of the body) to the transmitted alternating electrical current.

The one or more illustrative data storage devices 210 may be embodied as any type of devices configured for short-term or long-term storage of data such as, for example, memory devices and circuits, memory cards, hard disk drives, solid-state drives, or other data storage devices. Each data storage device 210 may include a system partition that stores data and firmware code for the data storage device 210. Each data storage device 210 may also include an operating system partition that stores data files and executables for an operating system.

The communication circuitry 212 may be embodied as any communication circuit, device, or collection thereof, capable of enabling communications over a network (not shown) between the compute device 110 and another device (e.g., another compute device, such as the protected system 140). The communication circuitry 212 may be configured to use any one or more communication technology (e.g., wired or wireless communications) and associated protocols (e.g., Ethernet, Bluetooth®, Wi-Fi®, WiMAX, etc.) to effect such communication.

The illustrative communication circuitry 212 includes a network interface controller (NIC) 214. The NIC 214 may be embodied as one or more add-in-boards, daughtercards, network interface cards, controller chips, chipsets, or other devices that may be used by the compute device 110 to connect with another device and transmit or receive data. In some embodiments, NIC 214 may be embodied as part of a system-on-a-chip (SoC) that includes one or more processors, or included on a multichip package that also contains one or more processors. In some embodiments, the NIC 214 may include a local processor (not shown) and/or a local memory (not shown) that are both local to the NIC 214. In such embodiments, the local processor of the NIC 214 may be capable of performing one or more of the functions of the controller 202 described herein. Additionally or alternatively, in such embodiments, the local memory of the NIC 214 may be integrated into one or more components of the compute device 110 at the board level, socket level, chip level, and/or other levels. The compute device 110 may additionally or alternatively include one or more peripheral devices 216. Such peripheral devices 216 may include any type of peripheral device commonly found in a compute device such as a display, speakers, and/or other input/output devices, interface devices, and/or other peripheral devices.

The protected system 140 may be embodied as any type of server or compute device capable of performing the functions described herein. The protected system 140 includes components typically found in a server compute device, such as a processor, memory, and communication circuit, the description of which is similar to the corresponding components of the compute device 110 and is not repeated herein for clarity of the description.

As described above, the compute device 110 and the protected system 140 are illustratively in communication via the network 150, which may be embodied as any type of wired or wireless communication network, including global networks (e.g., the Internet), local area networks (LANs) or wide area networks (WANs), cellular networks (e.g., Global System for Mobile Communications (GSM), 3G, Long Term Evolution (LTE), Worldwide Interoperability for Microwave Access (WiMAX), etc.), digital subscriber line (DSL) networks, cable networks (e.g., coaxial networks, fiber networks, etc.), or any combination thereof.

Figure 3:
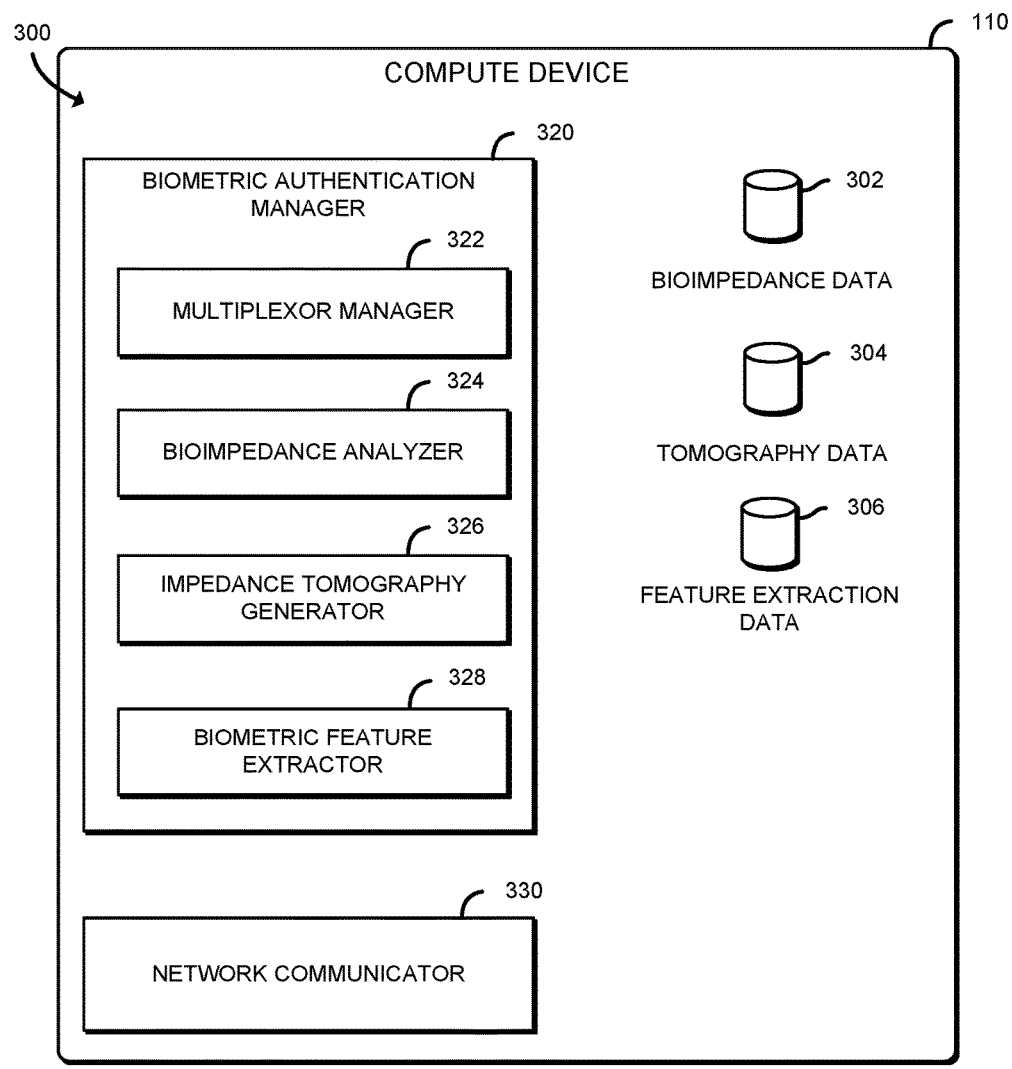
FIG. 3 is a simplified block diagram of an environment that may be established by a compute device of FIGS. 1 and 2.

Referring now to FIG. 3, in the illustrative embodiment, the compute device 110 may establish an environment 300 during operation. The illustrative environment 300 includes a biometric authentication manager 320 and a network communicator 330. Each of the components of the environment 300 may be embodied as hardware, firmware, software, or a combination thereof. As such, in some embodiments, one or more of the components of the environment 300 may be embodied as circuitry or a collection of electrical devices (e.g., biometric authentication manager circuitry 320, network communicator circuitry 330, etc.). It should be appreciated that, in such embodiments, one or more of the biometric authentication manager circuitry 320 or the network communicator circuitry 330 may form a portion of one or more of the controller 202, the biometric logic unit 222, the electrode subsystem 208, the main memory 204, the I/O subsystem 206, and/or other components of the compute device 110. In the illustrative embodiment, the environment 300 includes bioimpedance data 302 which may be embodied as any data indicative of frequencies at which an alternating current is to be transmitted through a section of the body of the user (e.g., a section of the user's wrist), measured bioimpedance (e.g., a phase and magnitude) to the alternating current at each frequency, indications of the pair of electrodes that transmitted the alternating current associated with a measurement, and the pair of electrodes associated with each bioimpedance measurement.

The illustrative environment 300 additionally includes tomography data 304 which may be embodied as any data indicative of tomographic images (e.g., images indicative of the electrical conductance and impedance of the physiology of the corresponding section of the user's body) generated from the bioimpedance data 302, identified positions of one or more fiducial markers (e.g., coordinates of the radius and ulna), and reference positions of the one or more fiducial markers usable to determine an amount of rotation (e.g., degrees, radians, etc.) to apply to the tomographic images to compensate for any inadvertent rotation of the electrodes 120, prior to performing a feature extraction process on the tomographic images. In the illustrative embodiment, the tomographic data 304 also includes the rotated versions of the tomographic images. Additionally, the illustrative embodiment 300 includes feature extraction data 306 which may be embodied as any data derived from the tomography data 304 and usable to uniquely identify the user. In the illustrative embodiment, the feature extraction data 306 may be embodied in a feature vector (e.g., an array of values). For example, the feature vector may include a set of statistical figures (e.g., average impedances over a range of frequencies at different positions in the tomographic images, a maximum impedance at one or more positions, a minimum impedance, etc.) that characterize the bioimpedance of the measured section of the user's body and uniquely identify the user.

In the illustrative environment 300, the biometric authentication manager 320, which may be embodied as hardware, firmware, software, virtualized hardware, emulated architecture, and/or a combination thereof as discussed above, is configured to transmit, with a pair of the electrodes 120, an alternating current through a section of the body of the user, measure, with another pair of the electrodes 120, a bioimpedance of the section of the body to the transmitted alternating current, generate a tomographic image as a function of the measured bioimpedance, identify a position of a fiduciary marker in the tomographic image, rotate the tomographic image to a predefined orientation as a function of the position of the fiduciary marker, extract biometric features from the rotated tomographic image, and perform authentication of the user as a function of the extracted biometric features. Further, in the illustrative embodiment, and as described in more detail herein, the biometric authentication manager 320 is configured to transmit the alternating current at multiple different frequencies, measure, for each frequency, the bioimpedance with multiple different pairs of the electrodes 120, and generate multiple tomographic images (e.g., one tomographic image for each frequency) from which to extract the biometric features. To do so, in the illustrative embodiment, the biometric authentication manager 320 includes a multiplexor manager 322, a bioimpedance analyzer 324, an impedance tomography generator 326, and a biometric feature extractor 328.

The multiplexor manager 322, in the illustrative embodiment, is configured to select a subset of the electrodes 120, such as a pair of adjacent electrodes 120, to transmit an alternating current at a selected frequency through the section of the user's body and to select another subset, such as a different pair of adjacent electrodes 120, or the same pair of electrodes 120, to measure the bioimpedance to the transmitted alternating current. As described in more detail herein, the multiplexor manager 322 may iteratively select different patterns of the electrodes 120 to measure the transmitted alternating current, enabling the compute device 110 to obtain sufficient data to generate a tomographic image indicative of the electrical conductance and impedance of the measured section of the user's body at each frequency.

In the illustrative embodiment, the bioimpedance analyzer 324 is configured to determine the frequency at which an alternating current is to be transmitted through the section of the user's body by two of the electrodes 120 and to analyze the resulting impedance with two other electrodes 120. The bioimpedance analyzer 324, in the illustrative embodiment, is configured to utilize a discrete Fourier transform on measurements received by the electrodes 120 to determine the magnitude ($|Z|$) and phase ($Z\theta$) of the impedance at the present frequency. The bioimpedance analyzer 324, in the illustrative embodiment, is configured to perform the determination for different patterns of the electrodes 120. In the illustrative embodiment, each pattern is an "adjacent-adjacent" pattern, in which electrodes 120 next to each other (e.g., electrodes 122, 124) are used to transmit the alternating current while other pairs of adjacent electrodes (e.g., electrode pair 126, 128, electrode pair 128, 130, electrode pair 130, 132, electrode pair 132, 134, electrode pair 134, 136, etc.) are used to measure the impedance. In the illustrative embodiment, the bioimpedance analyzer 324 repeats the measurement process for each of multiple frequencies to collect measurement data indicative of how different parts of the physiology respond differently (e.g., exhibit different impedances) to different frequencies.

The impedance tomography generator 326, in the illustrative embodiment, is configured to compute an impedance tomography (e.g., tomographic image) indicative of the conductivity of the section of the user's body along the plane in which the electrodes 120 are positioned. In the illustrative embodiment, the impedance tomography generator 326 generates a separate tomographic image for each frequency for which the impedance is measured. The biometric feature extractor 328, in the illustrative embodiment, is configured to locate, in each tomographic image, the positions of one or more fiduciary markers (e.g., bones or other identifiable portions of the physiology), and reorient the images according to reference positions (e.g., predefined positions of the fiduciary markers), such as by applying a linear transform to the tomographic images to rotate the located fiduciary markers to the reference positions. Subsequently, the biometric feature extractor 328 is configured to extract image-based features that form a vector (e.g., a feature vector) that is usable for biometric authentication (e.g., by comparing the generated feature vector to a reference feature vector and determining whether the differences between the two feature vectors satisfy one or more threshold differences).

It should be appreciated that each of the multiplexor manager 322, the bioimpedance analyzer 324, the impedance tomography generator 326, and the biometric feature extractor 328 may be separately embodied as hardware, firmware, software, virtualized hardware, emulated architecture, and/or a combination thereof. For example, the multiplexor manager 322 may be embodied as a hardware component, while the bioimpedance analyzer 324, the impedance tomography generator 326, and the biometric feature extractor 328 are embodied as virtualized hardware components or as some other combination of hardware, firmware, software, virtualized hardware, emulated architecture, and/or a combination thereof.

In the illustrative environment 300, the network communicator 330, which may be embodied as hardware, firmware, software, virtualized hardware, emulated architecture, and/or a combination thereof as discussed above, is configured to facilitate inbound and outbound network communications (e.g., network traffic, network packets, network flows, etc.) to and from the compute device 110, respectively, including requests to authenticate a user and responses to the requests (e.g., a response that includes a feature vector generated by the biometric authentication manager 320).

Figure 4:
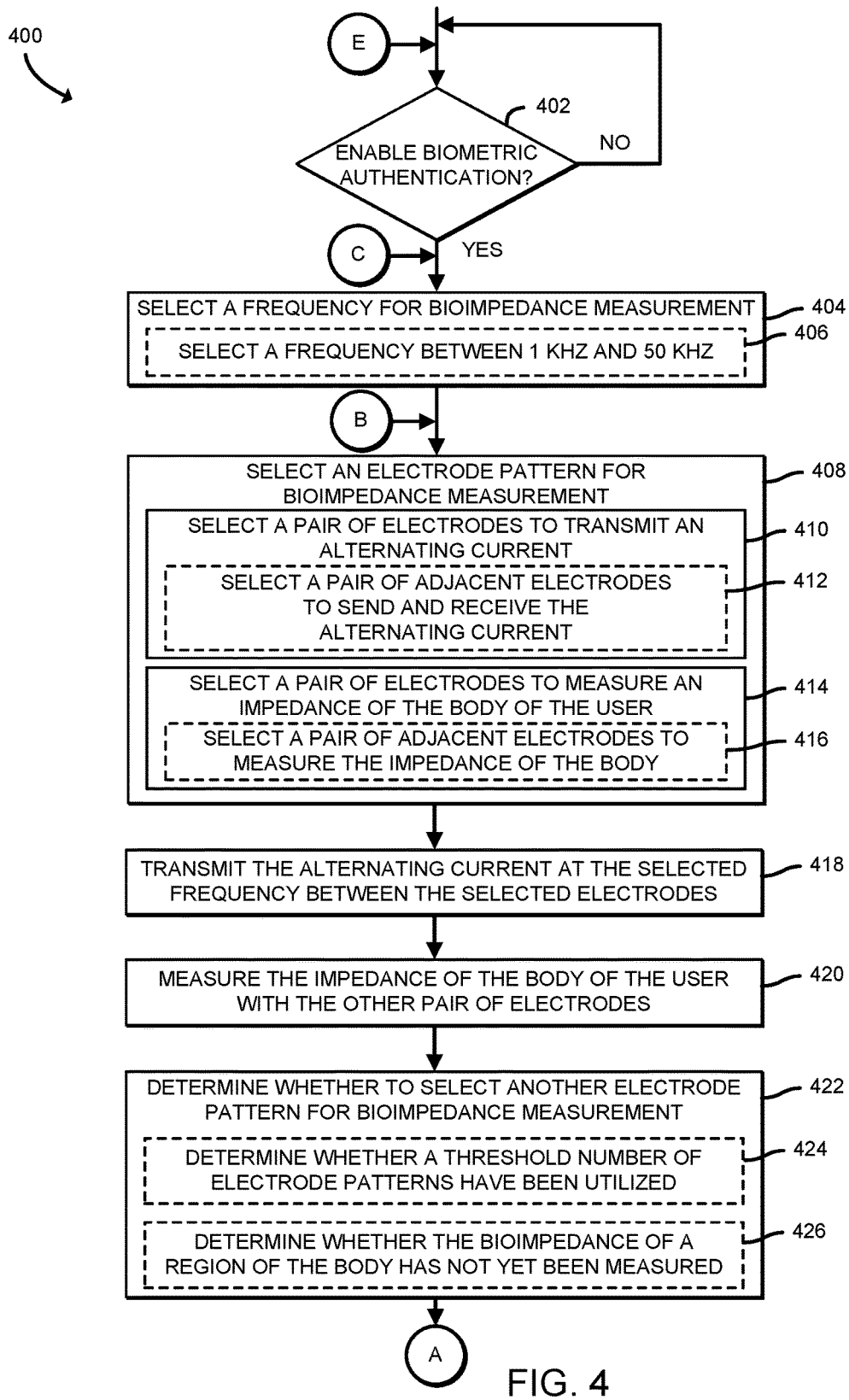
FIGS. 4-6 are a simplified flow diagram of at least one embodiment of a method for performing orientation-independent bioimpedance-based user authentication that may be performed by the compute device of FIGS. 1 and 2.

Referring now to FIG. 4, in use, the compute device 110 may execute a method 400 for performing orientation-independent bioimpedance-based user authentication. The method 400 begins with block 402 in which the compute device 110 determines whether to enable biometric authentication. In the illustrative embodiment, the compute device 110 determines to enable biometric authentication if the compute device 110 determines that the electrode subsystem 208 is operative and in contact with the skin of the user (e.g., by transmitting a test current and determining that the test current was conducted through the body of the user). In other embodiments, the compute device 110 determines whether to enable biometric authentication based on other factors. Regardless, in response to a determination to enable biometric authentication, the method 400 advances to block 404 in which the compute device 110 selects a frequency for bioimpedance measurement. In doing so, in the illustrative embodiment and as indicated in block 406, the compute device 110 selects a frequency between 1 kilohertz (kHz) and 50 kHz. For example, the compute device 110 may select one of a set number of representative frequencies across the range of 1 kHz to 50 kHz (e.g., frequencies that are 5 kHz apart). In some embodiments, the range of frequencies may be different (e.g., 1 kHz to 1 megahertz (MHz)).

Subsequently, in block 408, the compute device 110 selects an electrode pattern for bioimpedance measurement. In doing so, in the illustrative embodiment, the compute device 110 selects a pair of electrodes 120 to transmit an alternating current, as indicated in block 410. In the illustrative embodiment, the compute device 110 selects a pair of adjacent electrodes 120 to send and receive the alternating current, as indicated in block 412. For example, the compute device 110 may select the adjacent electrodes 122, 124 to send and receive the alternating current. In other embodiments, the compute device 110 may select a pair of electrodes 120 that are not adjacent to each other, to transmit the alternating current. Regardless, in selecting the electrode pattern, the compute device 110 additionally selects a pair of electrodes 120 to measure the impedance of the body of the user, as indicated in block 414. The pair of electrodes 120 to measure the impedance of the body may be a different pair than the pair of electrodes 120 from block 410, or may be the same pair. In doing so, the compute device 110 may select a pair of adjacent electrodes 120 to measure the impedance of the body, as indicated in block 416. For example, the compute device 110 may select adjacent electrodes 126, 128 to measure the impedance. In other embodiments, the compute device 110 may select a pair of electrodes 120 that are not adjacent to each other to measure the impedance.

Afterwards, the method 400 advances to block 418, in which the compute device 110 transmits the alternating current at the selected frequency between the selected electrodes 120 (e.g., the pair of electrodes 120 selected in block 410). Additionally, as indicated in block 420, the compute device 110 measures the impedance of the user's body with the other selected pair of electrodes 120 (e.g., the pair of electrodes 120 selected in block 414). It should be understood that while blocks 418 and 420 are shown in sequence in FIG. 4, the compute device 110, in the illustrative embodiment, measures the alternating current while the alternating current is being transmitted. After measuring the impedance of the body at the selected frequency, with the selected pattern of electrodes 120, the method 400 advances to block 422 in which the compute device 110 determines whether to select another electrode pattern for bioimpedance measurement. In doing so, the compute device 110 may determine whether a threshold number (e.g., five) of electrode patterns have been utilized, as indicated in block 424 and/or whether the bioimpedance of a region of the body where the electrodes 120 are in contact with the skin has not yet been measured, as indicated in block 426. For example, the compute device 110 may iteratively measure the bioimpedance with different pairs of electrodes in a clockwise order, around the wrist 170 of FIG. 1, and determine, if the electrode pair 134, 136 has not yet been used to measure the bioimpedance, to select the electrode pair 134, 136 for the next bioimpedance measurement. Subsequently, the method 400 advances to block 428 in which the compute device 110 determines the next course of action based on whether the compute device 110 determined to select another pattern.

Figure 5:
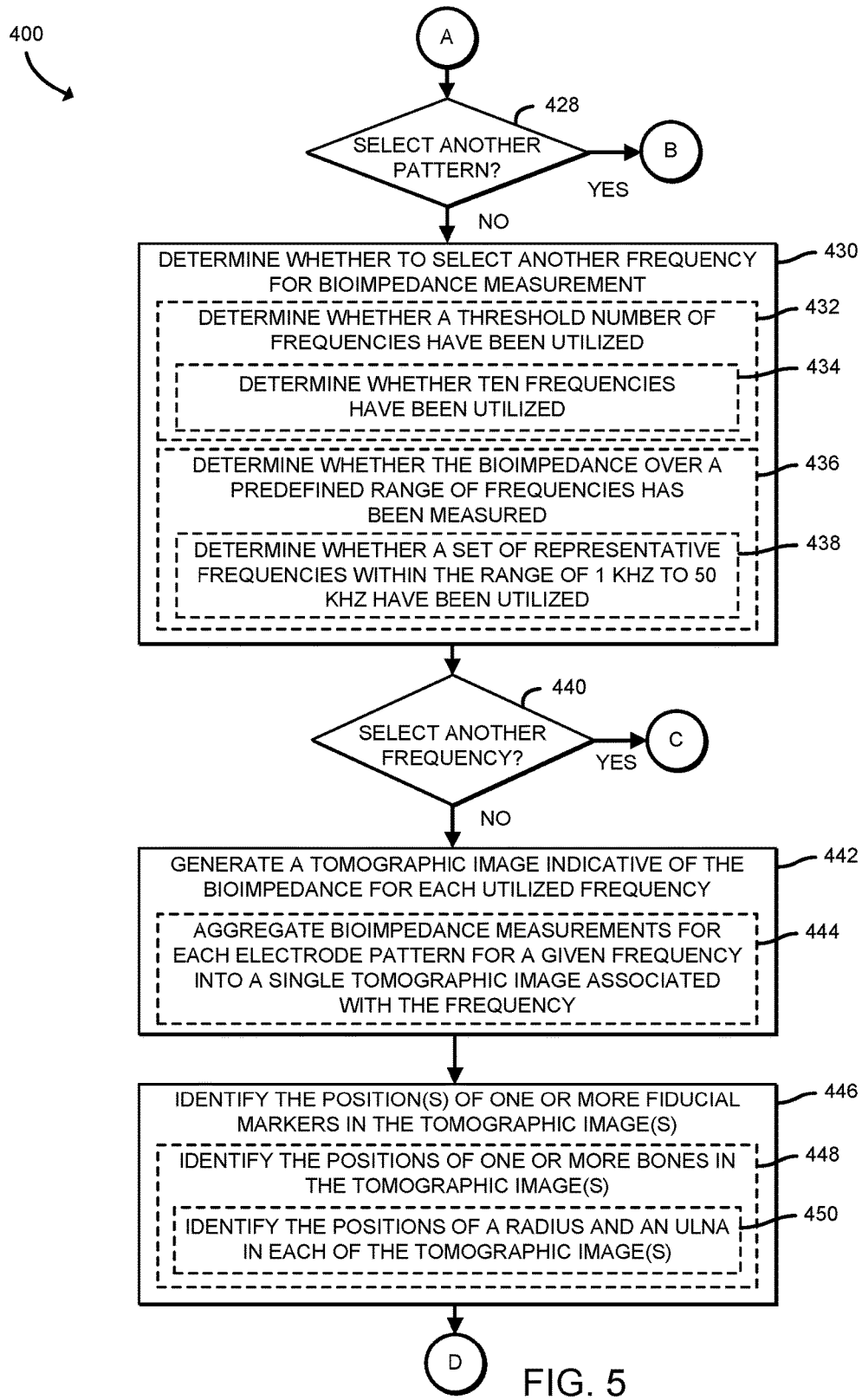

Referring now to FIG. 5, in block 428, the compute device 110 determines to select another pattern, the method 400 loops back to block 408 to select the next pattern for bioimpedance measurement at the selected frequency. Otherwise, the method 400 advances to block 430 in which the compute device 110 determines whether to select another frequency for bioimpedance measurement. In doing so, the compute device 110, in the illustrative embodiment, determines whether a threshold number of frequencies have been utilized, as indicated in block 432. For example, and as indicated in block 434, the compute device 110 determines whether ten different frequencies have been utilized. Additionally or alternatively, as indicated in block 436, the compute device 110 may determine whether the bioimpedance over a predefined range of frequencies has been measured. In doing so, and as indicated in block 438, the compute device 110 may determine whether a set of representative frequencies within the range of 1 kHz to 50 kHz have been utilized in the measurements. Afterwards, the method 400 advances to block 440 in which the compute device 110 determines the subsequent course of action in response to the determination made in block 430. In response to a determination to select another frequency, the method 400 loops back to block 404, in which the compute device 110 selects the next frequency for bioimpedance measurement. Otherwise, the method 400 advances to block 442, in which the compute device 110 generates a tomographic image indicative of the bioimpedance, and conversely, the conductance, of the section of the user's body for each utilized frequency (e.g., each frequency selected in each iteration of block 404). In doing so, in the illustrative embodiment, the compute device 110 aggregates the bioimpedance measurements (e.g., the bioimpedance data 302) for each frequency into a single tomographic image associated with the frequency, as indicated in block 444. For example, the compute device 110 may perform a discrete Fourier transform on the measurement data and generate a tomographic image in which the phase of the impedance in a given region is represented by one aspect of a pixel value, such as a color, and the magnitude of the impedance in the given region is represented by another aspect of the pixel value, such as an intensity of the color.

Subsequently, the method 400 advances to block 446 in which the compute device 110 identifies the positions of one or more fiducial markers in the tomographic images. In doing so, the compute device 110 may identify the positions of one or more bones in the tomographic images, as indicated in block 448. Further, in the illustrative embodiment, the compute device 110 may identify the positions of the radius bone and the ulna bone in each of the tomographic images, as indicated in block 450. The compute device 110 may do so by performing contour detection (i.e., detection of discontinuities in color or brightness) to detect shapes in the images and comparing the detected shapes to reference shapes indicative of known fiduciary markers (e.g., a cross sectional slice of the radius bone and a cross sectional slice of the ulna bone). Afterwards, the method 400 advances to block 452 of FIG. 6, in which the compute device 110 rotates each tomographic image to a predefined orientation as a function of the positions of the fiduciary markers.

Figure 6:
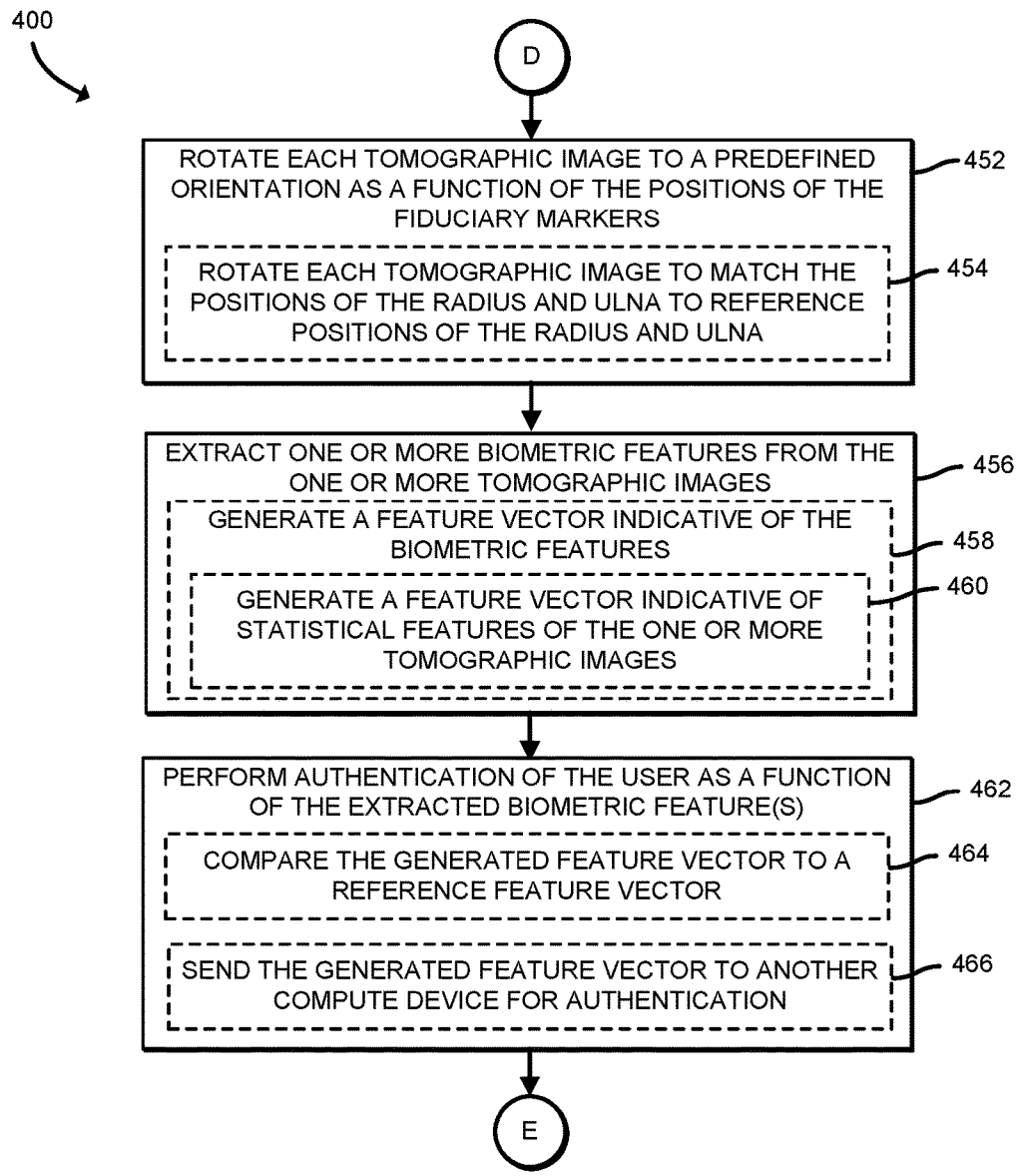

Referring now to FIG. 6, in rotating each tomographic image, the compute device 110 may rotate each tomographic image to match the positions of the radius bone and the ulna bone to reference positions of the radius and ulna bones, as indicated in block 454. For example, if the reference positions are oriented 30 degrees counterclockwise from the detected positions of the fiduciary markers, the compute device 110 may apply a linear transformation with a rotation matrix to rotate the pixel data of the tomographic images counterclockwise by 30 degrees. Subsequently, the method 400 advances to block 456, in which the compute device 110 extracts one or more biometric features from the tomographic images, as indicated in block 456. In doing so, the compute device 110 may generate a feature vector indicative of the biometric features, as indicated in block 458. Further, and as indicated in block 460, in generating the feature vector, the compute device 110 may generate a feature vector that is indicative of one or more statistical features of the one or more tomographic images (e.g., average pixel value for a position in the tomographic images over the range of frequencies, a maximum brightness at one or more positions in the tomographic images, a minimum brightness at one or more positions in the tomographic images, etc.). Subsequently, the method 400 advances to block 462, in which the compute device 110 performs authentication of the user as a function of the extracted biometric features. In doing so, the compute device 110 may compare the generated feature vector to a reference feature vector. For example, the compute device 110 may determine whether differences between the generated feature vector and the reference feature vector satisfy (e.g., are equal to or less than) a threshold difference. Alternatively, the compute device 110 may send the generated feature vector to another compute device (e.g., the protected system 140) for authentication (e.g., determining differences between the generated feature vector and a reference feature vector and determining whether the differences satisfy a threshold difference). Subsequently, the method 400 loops back to block 402 of FIG. 4, in which the compute device 110 determines whether to continue to enable biometric authentication.

It should be appreciated that while the compute device 110 is described above as performing the steps of the method 400, in some embodiments, the compute device 110 may perform the method 400 in cooperation with another compute device. As such, in some embodiments, the compute device 110 may offload a subset of the operations from the method 400 to a smart phone (not shown) in a personal area network with the compute device 110. For example, in some embodiments, the compute device 110 may perform a subset of the method 400, such as the collection of the bioimpedance data (e.g., blocks 404 through 440) and the generation of the tomographic images (e.g., block 442) and may transmit the tomographic images (e.g., tomography data 304) to a smartphone or other nearby compute device, to perform a different portion of the method 400 (e.g., tomographic image rotation, biometric feature extraction, and/or authentication).

EXAMPLES

Illustrative examples of the technologies disclosed herein are provided below. An embodiment of the technologies may include any one or more, and any combination of, the examples described below.

Example 1 includes a compute device to perform orientation-independent bioimpedance-based user authentication, the compute device comprising a plurality of electrodes usable to transmit an alternating current and measure a bioimpedance of a section of the body of a user; a biometric authentication manager to transmit, with a first pair of the electrodes, an alternating current through the section of the body of the user, measure, with a second pair of the electrodes, a bioimpedance of the section of the body to the transmitted alternating current, generate a tomographic image as a function of the measured bioimpedance, wherein the tomographic image is indicative of a physiology of the section of the body, identify a position of a fiduciary marker in the tomographic image, rotate the tomographic image to a predefined orientation as a function of the position of the fiduciary marker, extract one or more biometric features from the rotated tomographic image, and perform authentication of the user as a function of the extracted one or more biometric features.

Example 2 includes the subject matter of Example 1, and wherein to measure, with a second pair of the electrodes, a bioimpedance of the section of the body comprises to measure, with a second pair of the electrodes that is different from the first pair of the electrodes, the bioimpedance of the section of the body.

Example 3 includes the subject matter of any of Examples 1 and 2, and wherein the biometric authentication manager is further to measure, with multiple other pairs of the electrodes, the bioimpedance of the section of the body, prior to generation of the tomographic image.

Example 4 includes the subject matter of any of Examples 1-3, and wherein to transmit, with the first pair of the electrodes, the alternating current comprises to transmit, with a pair of adjacent electrodes, the alternating current.

Example 5 includes the subject matter of any of Examples 1-4, and wherein to measure, with the second pair of electrodes, the bioimpedance comprises to measure, with a pair of adjacent electrodes, the bioimpedance.

Example 6 includes the subject matter of any of Examples 1-5, and wherein to transmit the alternating current comprises to sequentially transmit the alternating current at each of a plurality of different frequencies and to measure the bioimpedance comprises to measure the bioimpedance with multiple different pairs of electrodes for each of the different frequencies.

Example 7 includes the subject matter of any of Examples 1-6, and wherein to generate a tomographic image comprises to generate a separate tomographic image associated with each of the different frequencies.

Example 8 includes the subject matter of any of Examples 1-7, and wherein to sequentially transmit the alternating current at each of a plurality of different frequencies comprises to sequentially transmit the alternating current at each of a plurality of frequencies over of a range of 1 kHz to 50 kHz.

Example 9 includes the subject matter of any of Examples 1-8, and wherein to sequentially transmit the alternating current at each of a plurality of frequencies over the range of 1 kHz to 50 kHz comprises to transmit the alternating current at each of ten frequencies over the range of 1 kHz to 50 kHz.

Example 10 includes the subject matter of any of Examples 1-9, and wherein to transmit the alternating current through the section of the body of the user comprises to transmit the alternating current through a section of a wrist of the user.

Example 11 includes the subject matter of any of Examples 1-10, and wherein to identify a position of a fiduciary marker in the tomographic image comprises to identify the positions of one or more bones in the wrist.

Example 12 includes the subject matter of any of Examples 1-11, and wherein to identify the positions of one or more bones in the wrist comprises to identify the positions of the radius and ulna bones.

Example 13 includes the subject matter of any of Examples 1-12, and wherein to generate a feature vector comprises to determine one or more statistical features of the tomographic image and store the one or more statistical features in the feature vector.

Example 14 includes the subject matter of any of Examples 1-13, and wherein to perform the authentication comprises to compare the generated feature vector to a reference feature vector.

Example 15 includes the subject matter of any of Examples 1-14, and further including a network communicator and wherein to perform the authentication comprises to send, with the network communicator, the feature vector to another compute device for authentication.

Example 16 includes the subject matter of any of Examples 1-15, and wherein the plurality of electrodes are equidistantly spaced from each other along a wristband.

Example 17 includes a method for performing orientation-independent bioimpedance-based user authentication, the method comprising transmitting, by a compute device and with a first pair of electrodes in a plurality of electrodes, an alternating current through a section of the body of the user; measuring, by the compute device and with a second pair of the electrodes, a bioimpedance of the section of the body to the transmitted alternating current; generating, by the compute device, a tomographic image as a function of the measured bioimpedance, wherein the tomographic image is indicative of a physiology of the section of the body; identifying, by the compute device, a position of a fiduciary marker in the tomographic image; rotating, by the compute device, the tomographic image to a predefined orientation as a function of the position of the fiduciary marker; extracting, by the compute device, one or more biometric features from the rotated tomographic image; and performing, by the compute device, authentication of the user as a function of the extracted one or more biometric features.

Example 18 includes the subject matter of Example 17, and wherein measuring, with a second pair of the electrodes, a bioimpedance of the section of the body comprises measuring, with a second pair of the electrodes that is different from the first pair of the electrodes, the bioimpedance of the section of the body.

Example 19 includes the subject matter of any of Examples 17 and 18, and further including measuring, by the compute device and with multiple other pairs of the electrodes, the bioimpedance of the section of the body, prior to generation of the tomographic image.

Example 20 includes the subject matter of any of Examples 17-19, and wherein transmitting, with the first pair of the electrodes, the alternating current comprises transmitting, with a pair of adjacent electrodes, the alternating current.

Example 21 includes the subject matter of any of Examples 17-20, and wherein measuring, with the second pair of the electrodes, the bioimpedance comprises measuring, with a pair of adjacent electrodes, the bioimpedance.

Example 22 includes the subject matter of any of Examples 17-21, and wherein transmitting the alternating current comprises sequentially transmitting the alternating current at each of a plurality of different frequencies and measuring the bioimpedance comprises measuring the bioimpedance with multiple different pairs of electrodes for each of the different frequencies.

Example 23 includes the subject matter of any of Examples 17-22, and wherein generating a tomographic image comprises generating a separate tomographic image associated with each of the different frequencies.

Example 24 includes the subject matter of any of Examples 17-23, and wherein sequentially transmitting the alternating current at each of a plurality of different frequencies comprises sequentially transmitting the alternating current at each of a plurality of frequencies over of a range of 1 kHz to 50 kHz.

Example 25 includes the subject matter of any of Examples 17-24, and wherein sequentially transmitting the alternating current at each of a plurality of frequencies over the range of 1 kHz to 50 kHz comprises transmitting the alternating current at each of ten frequencies over the range of 1 kHz to 50 kHz.

Example 26 includes the subject matter of any of Examples 17-25, and wherein transmitting the alternating current through the section of the body of the user comprises transmitting the alternating current through a section of a wrist of the user.

Example 27 includes the subject matter of any of Examples 17-26, and wherein identifying a position of a fiduciary marker in the tomographic image comprises identifying the positions of one or more bones in the wrist.

Example 28 includes the subject matter of any of Examples 17-27, and wherein identifying the positions of one or more bones in the wrist comprises identifying the positions of the radius and ulna bones.

Example 29 includes the subject matter of any of Examples 17-28, and wherein generating a feature vector comprises determining one or more statistical features of the tomographic image; and storing the one or more statistical features in the feature vector.

Example 30 includes the subject matter of any of Examples 17-29, and wherein performing the authentication comprises comparing the generated feature vector to a reference feature vector.

Example 31 includes the subject matter of any of Examples 17-30, and wherein performing the authentication comprises sending the feature vector to another compute device for authentication.

Example 32 includes one or more machine-readable storage media comprising a plurality of instructions stored thereon that, in response to being executed, cause a compute device to perform the method of any of Examples 17-31.

Example 33 includes a compute device for performing orientation-independent bioimpedance-based user authentication, the compute device comprising means for transmitting, with a first pair of electrodes in a plurality of electrodes, an alternating current through a section of the body of the user; means for measuring, with a second pair of the electrodes, a bioimpedance of the section of the body to the transmitted alternating current; means for generating a tomographic image as a function of the measured bioimpedance, wherein the tomographic image is indicative of a physiology of the section of the body; means for identifying a position of a fiduciary marker in the tomographic image; means for rotating the tomographic image to a predefined orientation as a function of the position of the fiduciary marker; means for extracting one or more biometric features from the rotated tomographic image; and means for performing authentication of the user as a function of the extracted one or more biometric features.

Example 34 includes the subject matter of Example 33, and wherein the means for measuring, with a second pair of the electrodes, a bioimpedance of the section of the body comprises means for measuring, with a second pair of the electrodes that is different from the first pair of the electrodes, the bioimpedance of the section of the body.

Example 35 includes the subject matter of any of Examples 33 and 34, and further including means for measuring, with multiple other pairs of the electrodes, the bioimpedance of the section of the body, prior to generation of the tomographic image.

Example 36 includes the subject matter of any of Examples 33-35, and wherein the means for transmitting, with the first pair of the electrodes, the alternating current comprises means for transmitting, with a pair of adjacent electrodes, the alternating current.

Example 37 includes the subject matter of any of Examples 33-36, and wherein the means for measuring, with the second pair of the electrodes, the bioimpedance comprises means for measuring, with a pair of adjacent electrodes, the bioimpedance.

Example 38 includes the subject matter of any of Examples 33-37, and wherein the means for transmitting the alternating current comprises means for sequentially transmitting the alternating current at each of a plurality of different frequencies and the means for measuring the bioimpedance comprises means for measuring the bioimpedance with multiple different pairs of electrodes for each of the different frequencies.

Example 39 includes the subject matter of any of Examples 33-38, and wherein the means for generating a tomographic image comprises means for generating a separate tomographic image associated with each of the different frequencies.

Example 40 includes the subject matter of any of Examples 33-39, and wherein the means for sequentially transmitting the alternating current at each of a plurality of different frequencies comprises means for sequentially transmitting the alternating current at each of a plurality of frequencies over of a range of 1 kHz to 50 kHz.

Example 41 includes the subject matter of any of Examples 33-40, and wherein the means for sequentially transmitting the alternating current at each of a plurality of frequencies over the range of 1 kHz to 50 kHz comprises means for transmitting the alternating current at each of ten frequencies over the range of 1 kHz to 50 kHz.

Example 42 includes the subject matter of any of Examples 33-41, and wherein the means for transmitting the alternating current through the section of the body of the user comprises means for transmitting the alternating current through a section of a wrist of the user.

Example 43 includes the subject matter of any of Examples 33-42, and wherein the means for identifying a position of a fiduciary marker in the tomographic image comprises means for identifying the positions of one or more bones in the wrist.

Example 44 includes the subject matter of any of Examples 33-43, and wherein the means for identifying the positions of one or more bones in the wrist comprises means for identifying the positions of the radius and ulna bones.

Example 45 includes the subject matter of any of Examples 33-44, and wherein the means for generating a feature vector comprises means for determining one or more statistical features of the tomographic image; and means for storing the one or more statistical features in the feature vector.

Example 46 includes the subject matter of any of Examples 33-45, and wherein the means for performing the authentication comprises means for comparing the generated feature vector to a reference feature vector.

Example 47 includes the subject matter of any of Examples 33-46, and wherein the means for performing the authentication comprises means for sending the feature vector to another compute device for authentication.

The invention claimed is:

1. A compute device to perform orientation-independent bioimpedance-based user authentication, the compute device comprising:
 a plurality of electrodes usable to transmit an alternating current and measure a bioimpedance of a section of the body of a user;
 a biometric authentication manager to transmit, with a first pair of the electrodes, an alternating current through the section of the body of the user, measure, with a second pair of the electrodes, a bioimpedance of the section of the body to the transmitted alternating current, generate a tomographic image as a function of the measured bioimpedance, wherein the tomographic image is indicative of a physiology of the section of the body, identify a position of a fiduciary marker in the tomographic image, rotate the tomographic image to a predefined orientation as a function of the position of the fiduciary marker, extract one or more biometric features from the rotated tomographic image, and perform authentication of the user as a function of the extracted one or more biometric features.

2. The compute device of claim 1, wherein to measure, with a second pair of the electrodes, a bioimpedance of the section of the body comprises to measure, with a second pair of the electrodes that is different from the first pair of the electrodes, the bioimpedance of the section of the body.

3. The compute device of claim 1, wherein the biometric authentication manager is further to measure, with multiple other pairs of the electrodes, the bioimpedance of the section of the body, prior to generation of the tomographic image.

4. The compute device of claim 1, wherein to transmit, with the first pair of the electrodes, the alternating current comprises to transmit, with a pair of adjacent electrodes, the alternating current.

5. The compute device of claim 1, wherein to measure, with the second pair of electrodes, the bioimpedance comprises to measure, with a pair of adjacent electrodes, the bioimpedance.

6. The compute device of claim 1, wherein to transmit the alternating current comprises to sequentially transmit the alternating current at each of a plurality of different frequencies and to measure the bioimpedance comprises to measure the bioimpedance with multiple different pairs of electrodes for each of the different frequencies.

7. The compute device of claim 6, wherein to generate a tomographic image comprises to generate a separate tomographic image associated with each of the different frequencies.

8. The compute device of claim 6, wherein to sequentially transmit the alternating current at each of a plurality of different frequencies comprises to sequentially transmit the alternating current at each of a plurality of frequencies over of a range of 1 kHz to 50 kHz.

9. The compute device of claim 8, wherein to sequentially transmit the alternating current at each of a plurality of frequencies over the range of 1 kHz to 50 kHz comprises to transmit the alternating current at each of ten frequencies over the range of 1 kHz to 50 kHz.

10. The compute device of claim 1, wherein to transmit the alternating current through the section of the body of the user comprises to transmit the alternating current through a section of a wrist of the user.

11. The compute device of claim 10, wherein to identify a position of a fiduciary marker in the tomographic image comprises to identify the positions of one or more bones in the wrist.

12. The compute device of claim 11, wherein to identify the positions of one or more bones in the wrist comprises to identify the positions of the radius and ulna bones.

13. One or more non-transitory machine-readable storage media comprising a plurality of instructions stored thereon that, when executed by a compute device, cause the compute device to:
 transmit, with a first pair of electrodes in a plurality of electrodes, an alternating current through a section of the body of a user;
 measure, with a second pair of the electrodes, a bioimpedance of the section of the body to the transmitted alternating current;
 generate a tomographic image as a function of the measured bioimpedance, wherein the tomographic image is indicative of a physiology of the section of the body;
 identify a position of a fiduciary marker in the tomographic image;
 rotate the tomographic image to a predefined orientation as a function of the position of the fiduciary marker;
 extract one or more biometric features from the rotated tomographic image; and
 perform authentication of the user as a function of the extracted one or more biometric features.

14. The one or more non-transitory machine-readable storage media of claim 13, wherein to measure, with a second pair of the electrodes, a bioimpedance of the section of the body comprises to measure, with a second pair of the electrodes that is different from the first pair of the electrodes, the bioimpedance of the section of the body.

15. The one or more non-transitory machine-readable storage media of claim 13, wherein the plurality of instructions, when executed, further cause the compute device to measure, with multiple other pairs of the electrodes, the bioimpedance of the section of the body, prior to generation of the tomographic image.

16. The one or more non-transitory machine-readable storage media of claim 13, wherein to transmit, with the first pair of the electrodes, the alternating current comprises to transmit, with a pair of adjacent electrodes, the alternating current.

17. The one or more non-transitory machine-readable storage media of claim 13, wherein to measure, with the second pair of the electrodes, the bioimpedance comprises to measure, with a pair of adjacent electrodes, the bioimpedance.

18. The one or more non-transitory machine-readable storage media of claim 13, wherein to transmit the alternating current comprises to sequentially transmit the alternating current at each of a plurality of different frequencies and to measure the bioimpedance comprises to measure the bioimpedance with multiple different pairs of electrodes for each of the different frequencies.

19. The one or more non-transitory machine-readable storage media of claim 18, wherein to generate a tomographic image comprises to generate a separate tomographic image associated with each of the different frequencies.

20. The one or more non-transitory machine-readable storage media of claim 18, wherein to sequentially transmit the alternating current at each of a plurality of different frequencies comprises to sequentially transmit the alternating current at each of a plurality of frequencies over of a range of 1 kHz to 50 kHz.

21. The one or more non-transitory machine-readable storage media of claim 20, wherein to sequentially transmit the alternating current at each of a plurality of frequencies over the range of 1 kHz to 50 kHz comprises to transmit the alternating current at each of ten frequencies over the range of 1 kHz to 50 kHz.

22. The one or more non-transitory machine-readable storage media of claim 13, wherein to transmit the alternating current through the section of the body of the user comprises to transmit the alternating current through a section of a wrist of the user.

23. A method for performing orientation-independent bioimpedance-based user authentication, the method comprising:
   transmitting, by a compute device and with a first pair of electrodes in a plurality of electrodes, an alternating current through a section of the body of the user;
   measuring, by the compute device and with a second pair of the electrodes, a bioimpedance of the section of the body to the transmitted alternating current;
   generating, by the compute device, a tomographic image as a function of the measured bioimpedance, wherein the tomographic image is indicative of a physiology of the section of the body;
   identifying, by the compute device, a position of a fiduciary marker in the tomographic image;
   rotating, by the compute device, the tomographic image to a predefined orientation as a function of the position of the fiduciary marker;
   extracting, by the compute device, one or more biometric features from the rotated tomographic image; and
   performing, by the compute device, authentication of the user as a function of the extracted one or more biometric features.

24. The method of claim 23, wherein measuring, with a second pair of the electrodes, a bioimpedance of the section of the body comprises measuring, with a second pair of the electrodes that is different from the first pair of the electrodes, the bioimpedance of the section of the body.

25. The method of claim 23, further comprising measuring, by the compute device and with multiple other pairs of the electrodes, the bioimpedance of the section of the body, prior to generation of the tomographic image.

* * * * *